(12) United States Patent
Stark et al.

(10) Patent No.: US 7,972,325 B2
(45) Date of Patent: Jul. 5, 2011

(54) DIRECT WAVEFRONT-BASED CORNEAL ABLATION TREATMENT PROGRAM

(75) Inventors: Lawrence W. Stark, Berkeley, CA (US); John K. Shimmick, Belmont, CA (US)

(73) Assignee: AMO Manufacturing, USA, LLC, Santa Ana, CA (US)

( * ) Notice: Subject to any disclaimer, the term of this patent is extended or adjusted under 35 U.S.C. 154(b) by 2160 days.

(21) Appl. No.: 10/006,992

(22) Filed: Dec. 6, 2001

(65) Prior Publication Data
US 2002/0135736 A1 Sep. 26, 2002

Related U.S. Application Data

(60) Provisional application No. 60/254,313, filed on Dec. 8, 2000.

(51) Int. Cl.
*A61F 9/008* (2006.01)
(52) U.S. Cl. ............................................. 606/5; 606/10
(58) Field of Classification Search .......... 356/124–126, 356/577–651; 606/5, 10–13; 607/88–93; 382/128; 250/217, 578.1, 234, 235; 378/4, 378/10; 351/205, 211, 212
See application file for complete search history.

(56) References Cited

U.S. PATENT DOCUMENTS

| | | | |
|---|---|---|---|
| 4,665,913 A | 5/1987 | L'Esperance, Jr. | |
| 4,692,027 A | 9/1987 | MacGovern et al. | |
| 4,804,269 A | 2/1989 | Elterman | |
| 5,054,907 A | 10/1991 | Sklar et al. | |
| 5,170,193 A | 12/1992 | McMillan et al. | |
| 5,258,791 A | 11/1993 | Penney et al. | |
| 5,646,791 A | 7/1997 | Glockler | |
| 5,683,379 A | 11/1997 | Hohla | |
| 5,713,892 A | 2/1998 | Shimmick | |
| 5,782,822 A * | 7/1998 | Telfair et al. | 606/5 |
| 6,000,800 A | 12/1999 | Webb et al. | |
| 6,011,625 A * | 1/2000 | Glass | 356/357 |
| 6,050,687 A | 4/2000 | Bille et al. | |
| 6,095,651 A | 8/2000 | Williams et al. | |
| 6,099,125 A | 8/2000 | Webb et al. | |
| 6,155,684 A | 12/2000 | Bille et al. | |
| 6,199,986 B1 | 3/2001 | Williams et al. | |
| 6,271,914 B1 | 8/2001 | Frey et al. | |
| 6,280,435 B1 * | 8/2001 | Odrich et al. | 606/5 |
| 6,299,311 B1 | 10/2001 | Williams et al. | |

(Continued)

OTHER PUBLICATIONS

Burns, "The spatially resolved refractometer" *J. Refract. Surgery* (2000) vol. 16:pp. S566-S569.

(Continued)

*Primary Examiner* — David Shay

(57) ABSTRACT

A method for measuring an optical system comprises transmitting an image with the optical system. Gradients of the optical system can be determined by separating the transmitted image with a lenslet array. An error-correcting change in the shape of the optical system can be mapped by integrating across the gradients. The change in elevation around the path is related to the accuracy of the gradient array. A system for measuring a wavefront of an eye includes an image source for projecting an image into the eye, lenslets, a detector for measuring angles of light rays of an optical surface of an eye, and a computer for mapping the errors of the eye. A tomographic wavefront map is made by deflecting the measurement path of the wavefront sensor. Aberrations are selected for treatment in response to an order of the aberration and a tissue structure corresponding to the aberration.

9 Claims, 14 Drawing Sheets

U.S. PATENT DOCUMENTS 6,331,059 B1    12/2001  Kudryashov et al.
6,373,918 B1 *   4/2002  Wiemker et al. ............... 378/62
6,486,943 B1 * 11/2002  Burns et al. .................. 356/124
6,563,105 B2 *   5/2003  Seibel et al. ................ 250/208.1
6,834,238 B1 * 12/2004  Hochman ..................... 382/128

OTHER PUBLICATIONS

Southwell "Wave-front estimation from wave-front slope measurements" *J. Opt. Soc. Am.* (1980) 70(8):998-1006.

Ragazzoni et al., "Adaptive-optics corrections available for the whole sky" *Nature* (2000) 403:54-56.

Supplementary European Search Report of Application No. 01987281, dated Nov. 27, 2008, 7 pages total.

Thibos, "Principles of Hartmann-Shack Aberrometry," J Refract Surg. Sep.-Oct. 2000;16(5):S563-565.

Dyson, "Photon noise and atmospheric noise in active optical systems", J. Opt. Soc. Am., vol. 65(5), pp. 551-558, May 1975.

Fried, "Least-square fitting a wave-front distortion estimate to an array of phase-difference measurements", J. Opt. Soc. Am., vol. 67(3), pp. 370-375, Mar. 1977.

Hudgin, "Wave-front reconstruction for compensated imaging", J. Opt. Soc. Am., vol. 67(3), pp. 375-378, Mar. 1977.

Hudgin, "Optimal wave-front estimation", J. Opt. Soc. Am., vol. 67(3), pp. 378-382, Mar. 1977.

Noll, "Phase estimates from slope-type wave-front sensors", J. Opt. Soc. Am., vol. 68, No. 1, pp. 139-140, Jan. 1978.

Born & Wolf, "Principles of Optics", $6^{th}$ Ed. (1980), pp. 374-383, 797.

Wallner, Wavefront Sensing, "Comparison of wavefront sensor configurations using optimal reconstruction and correction", Proc. SPIE vol. 351, pp. 42-53 (1982).

Wallner, "Optimal wave-front correction using slope measurements", J. Opt. Soc. Am., vol. 73(12), pp. 1771-1776, 1983.

Marsden and Tromba, Vector Calculus, Second Edition, 1981, pp. 96-103, 404-413, 448- 467, 484-485, and 586-587.

Article discussing life and death of first named inventor, Dr. Lawrence W. Stark, dated Nov. 1, 2004, 4 pages.

* cited by examiner

FIG. 11A
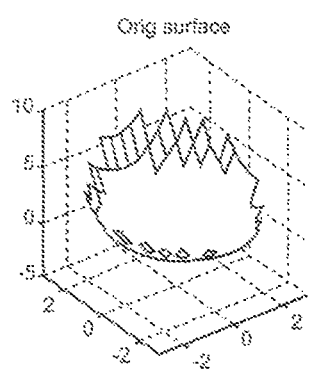
FIG. 11B
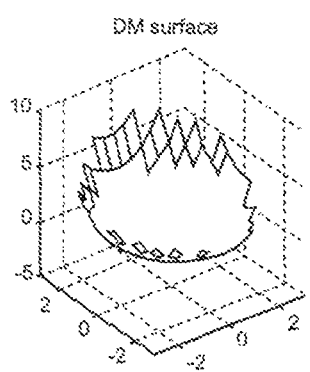
FIG. 11C
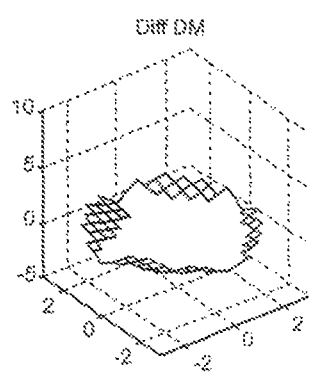
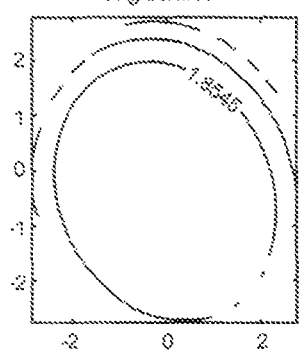
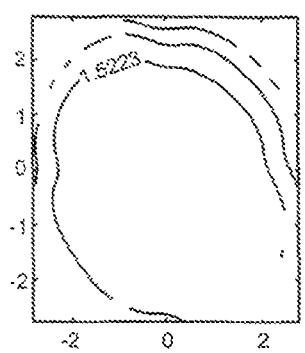
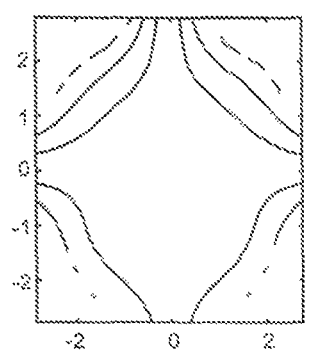
FIG. 11D
FIG. 11E
FIG. 11F

| j | n(ρ) | m(θ) | (C) | | Names | Order |
|---|---|---|---|---|---|---|
| 0 | 0 | 0 | (1) | $Z_0= 1$ <br> $Z_0= 1$ | Piston | Low |
| 0 | 0 | -1 | (3) | $Z_1= \rho \sin\theta$ <br> $Z_1= y$ | Tip | |
| 2 | 1 | 1 | (2) | $Z_2= \rho \sin\theta$ <br> $Z_2= x$ | Tilt | |
| 3 | 2 | -2 | (5) | $Z_3= \rho^2 \sin 2\theta$ <br> $Z_3= 2xy$ | Astig-45deg | Medium |
| 4 | 2 | 0 | (4) | $Z_4= 2\rho^2-1$ <br> $Z_4= 2(x^2 + y^2)-1$ | Sphere | |
| 5 | 2 | 2 | (6) | $Z_5= \rho^2 \sin 2\theta$ <br> $Z_5= x^2 - y^2$ | Astig-090deg | |
| 6 | 3 | -3 | (9) | $Z_6= \rho^3 \sin 3\theta$ <br> $Z_6= y(3x^2 - y^2)$ | Coma | |
| 7 | 3 | -1 | (7) | $Z_7= (3\rho^3-2\rho)\sin\theta$ <br> $Z_7= y(3(x^2 + y^2)-2)$ | | |
| 8 | 3 | 1 | (8) | $Z_8= (3\rho^3-2\rho)\cos\theta$ <br> $Z_8= x(3(x^2 + y^2)-2)$ | | |
| 9 | 3 | 3 | (10) | $Z_9= \rho^3 \cos 3\theta$ <br> $Z_9= x(x^2 - 3y^2)$ | Coma | |
| 10 | 4 | -4 | (15) | $Z_{10}= 4\rho^4 \sin 4\theta$ <br> $Z_{10}= 4xy(x^2 - y^2)$ | | |
| 11 | 4 | -2 | (13) | $Z_{11}= (4\rho^4-3\rho^2)\sin 2\theta$ <br> $Z_{11}= 2xy(4(x^2 + y^2)-3)$ | | |
| 12 | 4 | 0 | (11) | $Z_{12}= 6\rho^4-6\rho^2+1$ <br> $Z_{11}= 1+6[(x^2 + y^2)^2-(x^2+y^2)]$ | Spher Aberration | |
| 13 | 4 | 2 | (12) | $Z_{13}= (4\rho^4-3\rho^2)\cos 2\theta$ <br> $Z_{13}= 4(x^4 - y^4)-3(x^2 - y^2)$ | | |
| 14 | 4 | 4 | (14) | $Z_{14}= 4\rho^4 \cos 4\theta$ <br> $Z_{14}= x^4 + y^4 - 6x^2 y^2$ | | |

FIG. 12 ized by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

DIRECT WAVEFRONT-BASED CORNEAL ABLATION TREATMENT PROGRAM

CROSS-REFERENCES TO RELATED APPLICATIONS

The present application claims the benefit of priority from U.S. Provisional patent application Ser. No. 60/254,313 filed Dec. 8, 2000, the full disclosure of which is incorporated herein by reference.

BACKGROUND OF THE INVENTION

The present invention is generally related to measurement of optical systems. The invention provides devices, systems, and methods for measurement of optical errors of optical systems, and is particularly well-suited for determining a refractive correction of optical errors of the eye.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye. By customizing an ablation pattern based on wavefront measurements, it may be possible to correct minor refractive errors so as to reliably and repeatably provide visual acuities greater than 20/20.

Known methods for calculation of a customized ablation pattern using wavefront sensor data generally involves mathematically modeling an optical surface of the eye using expansion series techniques. More specifically, Zernike polynomials have been employed to model the optical surface. Coefficients of the Zernike polynomials are derived through known fitting techniques, and the refractive correction procedure is then determined using the shape of the optical surface eye indicated by the mathematical series expansion model.

Work in connection with the present invention suggests that the known methodology for calculation of a laser ablation treatment protocol based on wavefront sensor data may be less than ideal. The known Zernike polynomial modeling methods may result in errors or "noise" which can lead to a less than ideal refractive correction. Furthermore, the known surface modeling techniques are somewhat indirect, and may lead to unnecessary errors in calculation, as well as a lack of understanding of the physical correction to be performed.

In light of the above, it would be desirable to provide improved optical measurement techniques, particularly for use in measurements of the eye for refractive correction purposes.

SUMMARY OF THE INVENTION

In a first aspect, the invention provides a method for measuring optical tissues. The method comprises transmitting an image through the optical tissues. Local gradients of the optical tissues are determined across the optical system from the transmitted image. An error-correcting change in the shape of the optical system is mapped by integrating across the gradients.

The image will often be transmitted from a retina anteriorly through the optical tissues. The image on the retina may be generated by transmitting a source image posteriorly from a light source through the optical tissues and onto the retina. Small spots or points are particularly advantageous for use as the retinal images. The image can be transmitted onto the retina through a central region of the cornea which is smaller than the pupil of the eye. This can limit high-order optical errors in the image projected onto the retina, as the central portion of the cornea will often have a better optical shape than the peripheral portions. The mapping step may include derivation of a proposed change in optical tissue surface elevations so as to effect a desired change in optical properties. The method may further comprise modifying the optical tissue surface according to the proposed change.

The image transmitted by the optical tissues may be separated (for example, by a lenslet array) to define a plurality of beamlets. The gradients can comprise an array of gradients corresponding to portions of an optical surface, each beamlet being transmitted by an associated lenslet according to the corresponding gradient. The integrating step may comprise integrating about a closed integration path across the gradient array. An accuracy of at least one of the gradients of the gradient array may be determined by calculating a change in elevation along such a closed integration path. Closed paths may be defined by center-to-center integrations between the surface portions associated with the gradients, but will preferably be defined using initial locations upon the optical surface between the gradient defining portions, so that integration across a portion can be performed based directly upon its associated gradient.

In some embodiments, the transmitted image may be adjusted with an adaptive optical element so as to compensate for at least some of the errors of the optical system. For example, when a source image is projected onto the retina through corneal tissues, a deformable mirror may adjust the source image so that the image, as it appears on the retina, is well defined.

Optionally, an elevation map of an optical surface of the optical system may be generated directly in the mapping step, without deriving coefficients of a series expansion which mathematically approximates the optical surface. This can avoid the errors which may be induced by use of Zernike polynomials and other series expansion techniques.

In another aspect, the invention provides a system for diagnosing an eye of a patient. The eye has a retina and optical tissues. The system comprises an image source arranged to direct an image through the optical tissues and onto the retina. A wavefront sensor is oriented to sense the image as transmitted anteriorly by the optical tissue. The wavefront sensor generates signals indicating gradients across the optical tissues. A processor includes an integration module configured for integrating among the gradients to determine a map for correction of the optical tissues.

Preferably, the processor directly determines a surface elevation map of a surface of the eye, without generating coefficients of a series expansion which mathematically approximates the surface. The integration module may comprise hardware, software, firmware, and/or a combination thereof.

In a further aspect, the invention provides a method for measuring a tomographic wavefront error map of an eye. A light measurement path is deflected to a first angular orientation relative to the eye, and the optical tissue surface of the eye is measured at the first angular orientation. The light measurement path is deflected to a second angular orientation, at which a second optical tissue surface is measured. The tomographic wavefront error map of the eye is calculated from the sequential optical tissue surfaces. The tomographic map comprises a plurality of localized optical tissue surfaces at different depths inside the eye. The method may include repeating the steps of deflecting and measuring, and may also include forming a light structure having a feature on the retina of the eye.

In a still further aspect, the invention provides a method of selecting an aberration of an eye for treatment. By calculating a tomographic wavefront error map of an eye, the localized optical tissue surfaces are associated with a corresponding tissue structure of the eye. An aberration is selected for treatment in response to the tissue structure corresponding to the aberration. Aberrations that have been selected for treatment are combined to form an optical treatment surface. An aberration corresponding to a corneal tissue structure may be included in a treatment, and an aberration corresponding to a lenticular tissue structure may be excluded from the treatment. The aberrations selected for treatment may comprise a subset of the measured aberrations of the eye.

In yet a further aspect, the invention provides a method of measuring a wavefront of an eye. A light measurement path of a wavefront sensor is deflected to a first angular orientation relative to the eye, and a first optical tissue surface of the eye is measured. The light measurement path is deflected to a second angular orientation, and a second optical tissue surface of the eye is measured. The wavefront error map of the eye is calculated from the sequential optical tissue measurements. The method may include repeating the steps of deflecting and measuring to obtain a plurality of optical tissue surface measurements. The method may also include forming a light structure with a feature on the retina and displacing the light structure from a first position to a second position so that a feature of the light structure in the second position is resolvable from the feature of structure in the first position.

BRIEF DESCRIPTION OF THE DRAWINGS

FIGS. 11A-11F graphically illustrate simulated wavefront data comparing direct calculation of an optical surface to an original theoretical surface derived from a series expansion model, according to the flow diagram of FIG. 10.

FIG. 12 lists low and medium order Zernike polynomials, and identifies selected Zernike polynomials for use in a series expansion model of an optical surface.

DESCRIPTION OF THE SPECIFIC EMBODIMENTS

The present invention is particularly useful for enhancing the accuracy and efficacy of laser eye surgical procedures, such as photorefractive keratectomy (PRK), phototherapeutic keratectomy (PTK), laser in situ keratomileusis (LASIK), and the like. Preferably, the present invention can provide enhanced optical accuracy of refractive procedures by improving the methodology for deriving a corneal ablation or other refractive treatment program. Hence, while the system and methods of the present invention are described primarily in the context of a laser eye surgery system, it should be understood that the techniques of the present invention may be adapted for use in alternative eye treatment procedures and systems such as radial keratotomy, intraocular lenses, corneal ring implants, collagenous corneal tissue thermal remodeling, and the like.

The techniques of the present invention can be readily adapted for use with existing laser systems, wavefront sensors, and other optical measurement devices. By providing a more direct (and hence, less prone to noise and other error) methodology for correcting errors of an optical system, the present invention may facilitate sculpting of the cornea so that treated eyes regularly exceed the normal 20/20 threshold of desired vision.

Wavefront sensors will typically measure aberrations and other optical characteristics of an entire optical tissue system. The data from such a wavefront sensor may be used to generate an optical surface from an array of optical gradients. It should be understood that the optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein the terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure). As used herein, the term image may encompass a point of light or a small spot of light.

Figure 1:
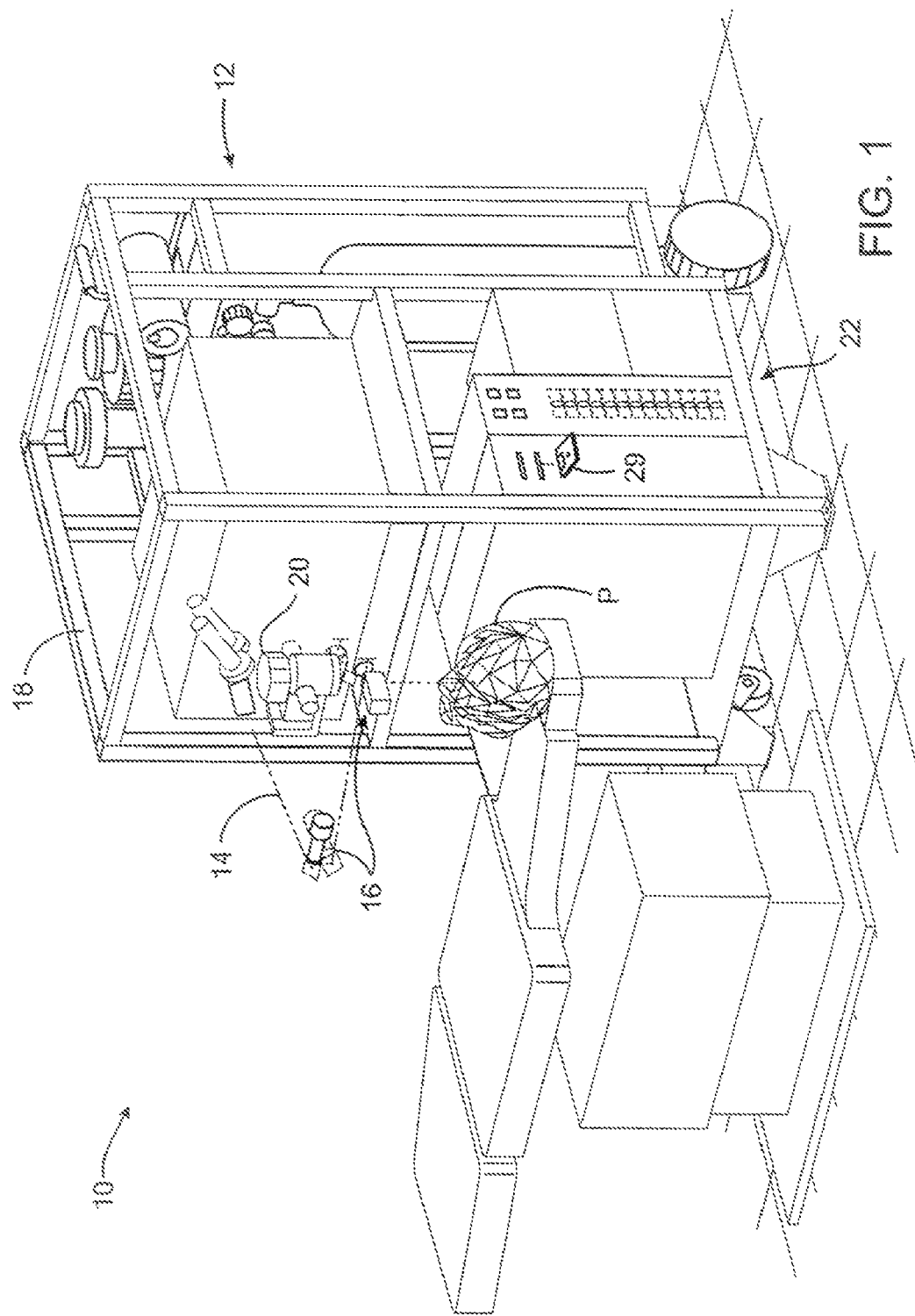
FIG. 1 is a perspective view of a laser ablation system.

Referring now to FIG. 1, a laser eye surgery system 10 of the present invention includes a laser 12 that produces a laser beam 14. Laser 12 is optically coupled to laser delivery optics 16, which direct laser beam 14 to an eye of patient P. A delivery optics support structure (not shown here for clarity) extends from a frame 18 supporting laser 12. A microscope 20 is mounted on the delivery optics support structure, the microscope often being used to image a cornea of an eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible media 29 in the form of a treatment table, and the treatment table may be adjusted according to feedback input into processor 22 from an automated image analysis system (manually input into the processor by a system operator) in response to feedback data provided from an ablation monitoring system feedback system. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor 22 will include the memory boards and other standard components of modern computer systems for storing and executing this code. Tangible storage media 29 may optionally embody wavefront sensor data, wavefront gradients, a wavefront elevation map, a treatment map, and/or an ablation table.

Figure 2:
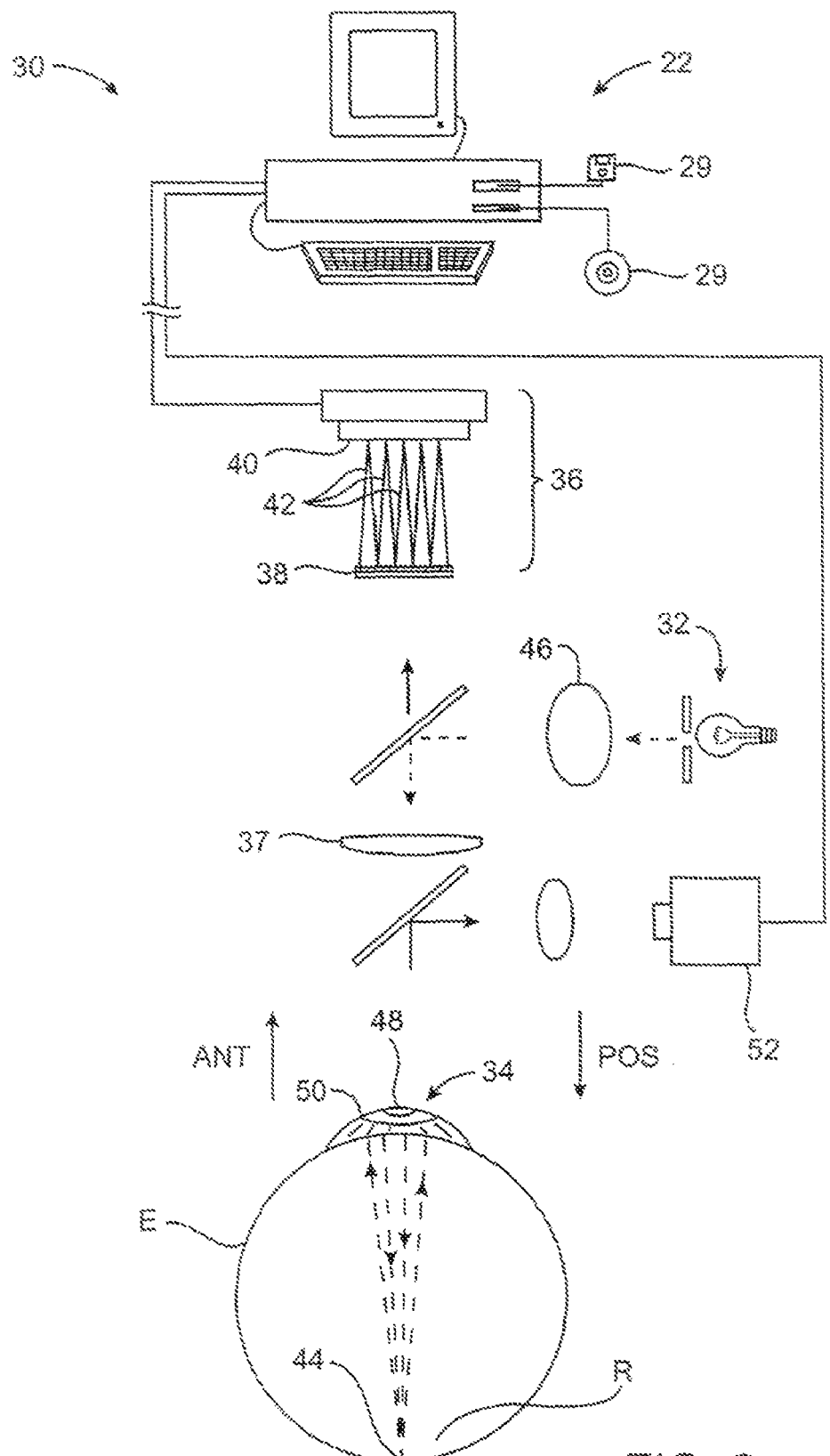
FIG. 2 schematically illustrates a method and system for directly determining a corneal ablation treatment prescription or program from wavefront sensor data.

Referring now to FIG. 2, an exemplary wavefront sensor system 30 is schematically illustrated in simplified form. In very general terms, wavefront system 30 includes an image source 32 which projects a source image through optical tissues 34 of eye E and so as to form an image 44 upon a surface of retina R. The image from retina R is transmitted by the optical system of the eye (specifically, optical tissues 34) and imaged onto a wavefront sensor 36 by system optics 38. The wavefront sensor 36 communicates signals to computer 22 for determination of a corneal ablation treatment program. Computer 22 may be the same computer which is used to direct operation of the laser surgery system 10, or at least some or all of the computer components of the wavefront sensor system and laser surgery system may be separate. Data from wavefront sensor 36 may be transmitted to a separate laser system computer via tangible media 29, via an I/O port, via an networking connection such as an intranet or the Internet, or the like.

Wavefront sensor 36 generally comprises a lenslet array 38 and an image sensor 40. As the image from retina R is transmitted through optical tissues 34 and lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics may decrease lower order optical errors by compensating for spherical and/or cylindrical errors of optical tissues 34. Higher order optical errors of the optical tissues may also be compensated through the use of an adaptive optic element, such as a deformable mirror. Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have well-defined and accurately formed image 44 on retina R.

While the method of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront sensor system 30 by focusing on a fixation target, as described in U.S. Pat. No. 6,004,313, the full disclosure of which is incorporated herein by reference. By varying a focal position of the fixation target as described in that reference, optical characteristics of the eye may be determined while the eye accommodates or adapts to image a field of view at a varying distance. Further alternatives include rotating of the eye by providing alternative and/or moving fixation targets within wavefront sensor system 30.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues, as will also be described hereinbelow.

Figure 3:
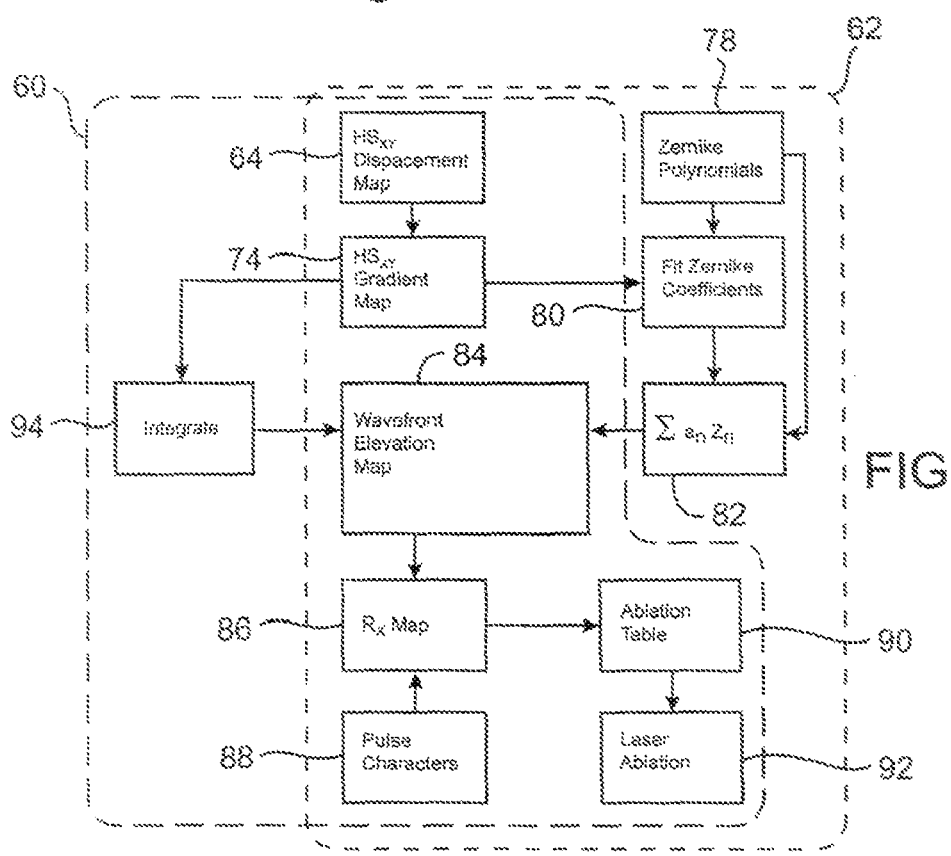
FIG. 3 is a flow chart schematically illustrating a method for directly determining a corneal ablation treatment program using wavefront sensor data, as well as a method for indirectly determining a corneal ablation treatment program using a mathematical series expansion model of a corneal tissue surface derived from wavefront sensor data.

Referring now to FIG. 3, the advantages of the direct wavefront-based corneal ablation treatment method 60 may be understood, particularly when compared to a treatment method relying on an expansion series for modeling of corneal tissue 62. However, it should be understood that these two methods are not contradictory or mutually exclusive, and may be combined as shown.

Figure 4:
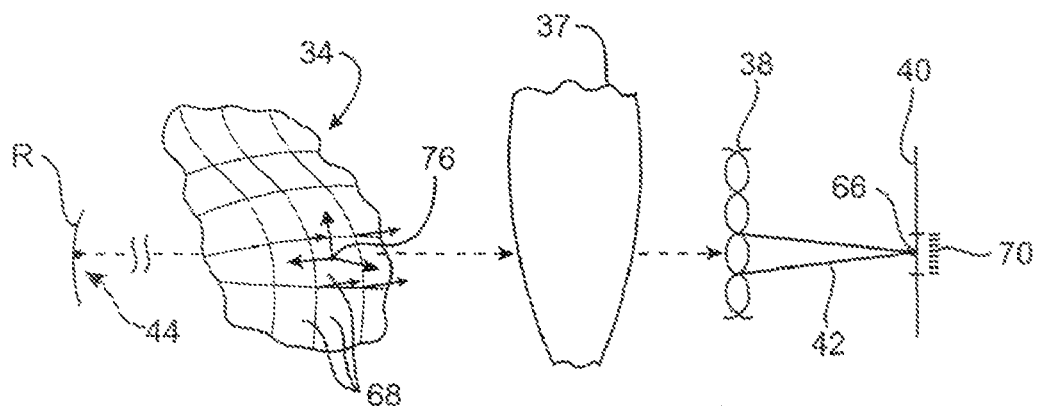
FIG. 4 schematically illustrates a method for determining gradients of an optical system using wavefront sensor data.

In series expansion method 62, a Hartmann-Shack displacement map 64 is generated from the data provided by wavefront sensor 36. Generation of such a displacement map can be understood with reference to FIGS. 4 and 6. As illustrated in FIG. 4, image 44 on retina R is transmitted through optical tissue 34, optics 37, and lenslet array 38 so that each beamlet is imaged onto image sensor 40. The location 70 of the transmitted image 66 upon imaging sensor 40 generally indicates optical properties of an associated portion 68 of optical tissue 34. Each lenslet of lenslet array 38 corresponding to a portion 68 of optical tissue 34 within pupil 50 (see FIG. 2), as well as to the beamlet which transfers information from the optical system onto the sensor surface. Position 70 will often be sensed as a pixel location of a point light signal resulting from imaging of a point light source.

Figure 6:
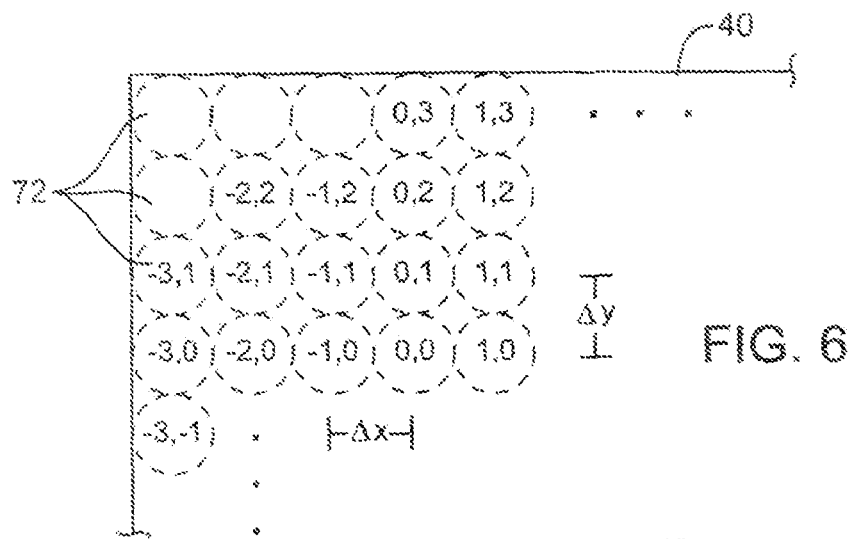
FIG. 6 schematically illustrates an arrangement of data array generated by a wavefront sensor that can be used for calculation of a gradient array.

Referring now to FIG. 6, each lenslet 38 may also have a corresponding region 72 upon sensor 40. Each sensor region/lenslet will have an associated coordinate reference as schematically illustrated in FIG. 6. The spacing between lenslets and/or sensor regions is indicated by $\Delta x$ and $\Delta y$. The array of positions 70 generated by separating transmitted image 66 with each lenslet of the lenslet array defines the displacement map 64.

Referring once again to FIG. 3, from Hartmann-Shack displacement map 64 it is possible to calculate a Hartmann-Shack gradient map 74, as can be understood with reference to FIG. 4. Each portion 68 of optical tissue 34 includes a tissue surface having a local gradient 76. Local gradients 76 will have a significant impact on the location 70 of associated portion of the transmitted image 66 as separated on sensor 40, and the gradient can readily be derived from location 70. Gradient map 74 may comprise an array of the localized gradients 76 as calculated from each location 70 for each lenslet.

When the gradient map 74 is to be used to derive a mathematical model of the tissue surface using series expansion techniques, the gradient map and selected expansion series 78 are used to derive appropriate expansion series coefficients 80. A particularly beneficial form of a mathematical series expansion for modeling the tissue surface are Zernike polynomials. The coefficients $a_n$ for each Zernike polynomial $Z_n$ may, for example, be determined using a standard least squares fit technique. The number of Zernike polynomial coefficients $a_n$ may be limited (for example, to about 27 coefficients).

While generally considered convenient for modeling of the optical surface so as to generate an elevation map, Zernike polynomials (and perhaps all series expansions) can introduce errors. Nonetheless, combining the Zernike polynomials with their coefficients and summing 82 allows a wavefront elevation map 84 to be calculated.

A treatment program map 86 may be calculated from the wavefront elevation map so as to remove the regular (spherical and/or cylindrical) and irregular errors of the optical tissues. By combining the treatment program 86 with a laser ablation pulse characteristics 88 of a particular laser system, a table 90 of ablation pulse locations, sizes, shapes, and/or numbers can be developed. An exemplary method and system for preparing such an ablation table is described in co-pending U.S. patent application Ser. No. 60/189,633 filed on Mar. 14, 2000 and entitled "Generating Scanning Spot Locations for Laser Eye Surgery," the full disclosure of which is incorporated herein by reference. Ablation table 90 may optionally be optimized by sorting of the individual pulses so as to avoid localized heating, minimize irregular ablations if the treatment program is interrupted, and the like. The eye can then be ablated according to the treatment table 90 by laser ablation 92.

In direct treatment method 60, the Hartmann-Shack gradient map 74 is used directly to calculate wavefront elevation map 84 by integrating 94 between the elements of the gradient map or array. This integration process can be generally understood with reference to FIG. 5.

Figure 5:
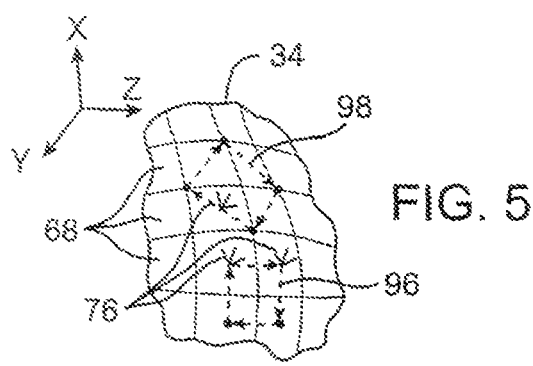
FIG. 5 schematically illustrates alternative closed integration paths for integrating across a gradient array so as to derive an elevation map and/or verify accuracy of the wavefront sensor data.

As illustrated in FIG. 5, relative heights or locations along the z (visual or anterior-posterior) axis of the different portions 68 of optical surface 34 may be determined by integrating along an integration path between adjacent regions, with the regions defined by the lenslet array. A first possible integration path 96 might determine changes in height by integrating gradients 76 along a path from a center of a first region to a center of a second region. By continuing such center-to-center integrations along a closed integration path (often along two or more separate paths between common starting and ending locations), a determination may be made of the accuracy of the calculated elevations. An analogy is that if you are standing on a hill, if you walk a closed path back to the starting point, you should end up at the same elevation at which you started. A number of open and/or closed integration paths may be followed across optical tissue 34 so as to determine the relative elevations throughout the gradient map.

One disadvantage of the center-to-center integration path 96 is that each integration step from a first portion 68 to a second adjacent portion 68 will have a total change in elevation affected by two different gradients: the first half of the integration path will remain on the first portion 68 which will be dominated by the gradient 76 of that portion. The second half of the integration path to the adjacent path center will have an elevation change predominately varying with the gradient of the second portion. To avoid having to manipulate multiple gradients along a single leg of the integration path, an edge-to-edge integration path 98 provides integration path steps whose change in elevation will be dominated entirely by a single gradient. However, note that the edge-to-edge integration path 98 may have longer path lengths than the center-to-center path 96.

Figure 6A:
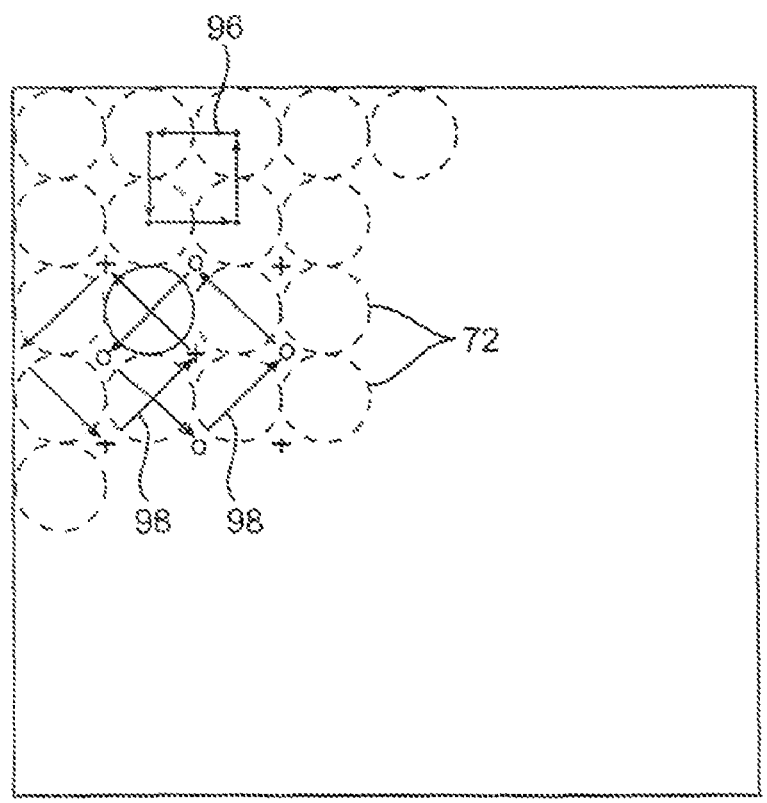
FIG. 6A illustrates alternative integration paths for deriving an elevation map from wavefront gradients.

Referring now to FIGS. 5 and 6A, integration along two separate integration paths from a common starting point a common ending point is shown to define a closed integration loop. Beginning at center point of region 0,0 we know that the elevation f(0,0) is equal to a constant c. Integrating along two separate paths from 0,0 to 1,1 may be performed as follows:

$$f(0, 1) = f(0, 0) + \frac{\partial f}{\partial x}\bigg|_{00\to 01} \Delta x + \frac{\partial f}{\partial x}\bigg|_{00\to 01} \Delta y \quad (1A)$$

$$f(1, 0) = f(0, 0) + \frac{\partial f}{\partial x}\bigg|_{00\to 10} \Delta x + \frac{\partial f}{\partial y}\bigg|_{00\to 10} \Delta y \quad (1B)$$

$$f(1, 1) = f(0, 1) + \frac{\partial f}{\partial x}\bigg|_{01\to 11} \Delta x + \frac{\partial f}{\partial y}\bigg|_{01\to 11} \Delta y \quad (1C)$$

$$f(1, 1) = f(1, 0) + \frac{\partial f}{\partial x}\bigg|_{10\to 11} \Delta x + \frac{\partial f}{\partial y}\bigg|_{10\to 11} \Delta y \quad (1D)$$

The elevation at a given point will, of course, be the same regardless of the path taken to arrive at that point. In other words, the elevation of a point on a surface is independent of the integral. If the wavefront has a frequency cut-off, then neighboring points will enable reconstruction of a missing or noisy point. This allows the line path integrals over the matrix of points to be used to develop estimates based on the eccentricity and magnitude of the Hartmann-Shack data, so long as the Hartmann-Shack data points from adjacent lenslets are not independent estimators (as they would be if they are separated sufficiently so as to have little redundancy). This requirement may be mathematically formalized as the Lipschitz criteria. The Lipschitz criteria is an inequality that guarantees a unique solution to the differential equation y' is equal to f(x,y).

By integrating the elevation of a point along several differing paths, it is possible to detect bad Hartmann-Shack data along a path. If the elevation calculated along one path is significantly different from the elevation calculated by a plurality of other paths, then a measurement along the one significant path giving a significantly different elevation may be incorrect.

As mentioned above regarding FIG. 5, an alternative technique for integrating the wavefront data is to select a path that travels only over one region corresponding to a single lenslet during an integration path step. Such single gradient edge-to-edge paths 98 are further illustrated in FIG. 6A, together with a center-to-center path 96. Once again, each integration path step in center-to-center path 96 will involve the use of gradients from two adjacent regions 72.

Figure 7A:
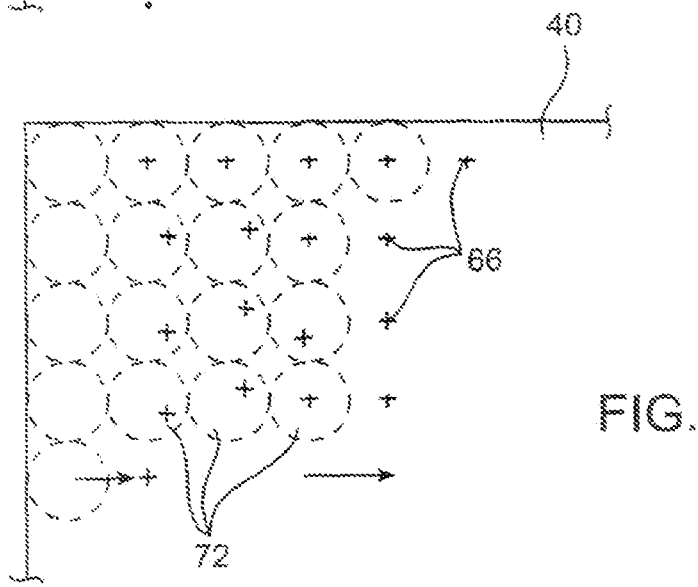
FIGS. 7A-7C schematically illustrate registration of the wavefront sensor data with the optical tissues of the eye using a pupil camera of the diagnostic system.
Figure 7B:
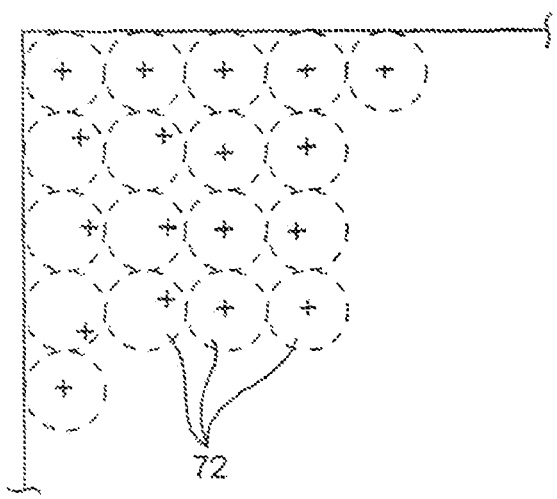

Referring now to FIGS. 7A and 7B, transmitted image 66 for each associated region 72 will vary in position according to the associated element of the Hartmann-Shack gradient array or map. In fact, where the optical tissue surface 34 is at a significant tilt, transmitted image 66 from a particular lenslet of lenslet array 38 may be disposed beyond the associated sensor region 72. This is schematically illustrated in FIG. 7A, in which transmitted images 66 are offset by an amount greater than ½ ($\Delta x$) from their associated sensor region centers.

To accurately measure the tilt of the wavefront, each transmitted image 66 from lenslet array 38 should be appropriately registered to its associated lenslet and sensor region. This registration may be performed by measuring the position of the pupil with pupil camera 52, as illustrated in FIG. 2.

Figure 7C:
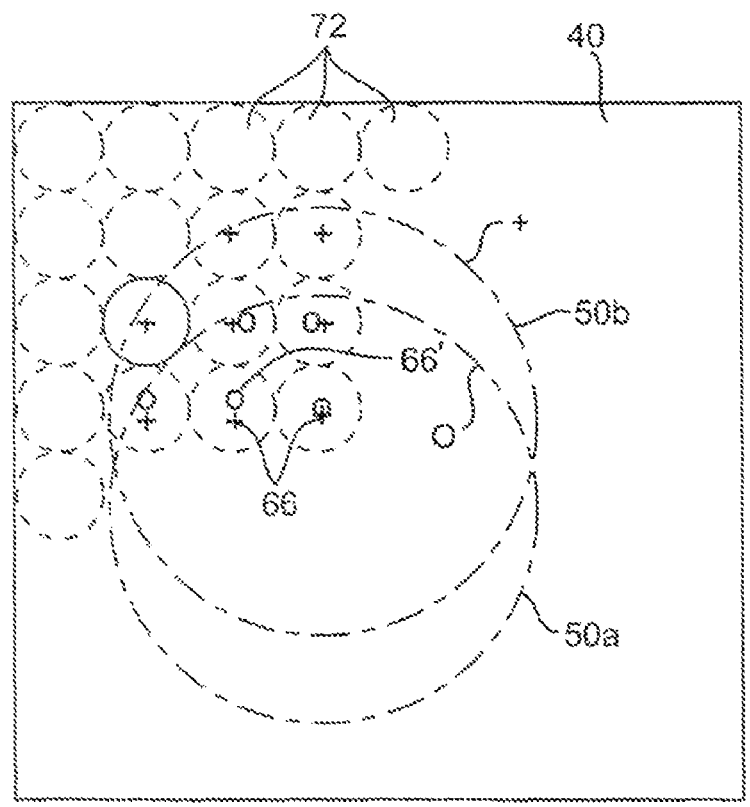

As can be understood with reference to FIG. 7C, the pupil location 50a, 50b may be combined with the Hartmann-Shack data to ensure that transferred image 66 is appropriately registered with the associated lenslet. More specifically, the pupil and iris are conjugate with the wavefront sensor array. For a measured position of the pupil relative to sensor 36, the position of the image of the pupil, and of the edge of the pupil on the Hartmann-Shack lenslet array, can be calculated. From this calculated edge position, each transferred image 66 may be confidently associated with a particular lenslet. For example, where the pupil is located at position 50a, the "o" transferred images 66' within the edge of the pupil will be formed upon sensor 40. As the location of the upper edge of the pupil and the uppermost transferred images 66' are known, each transferred image 66' may be appropriately registered with its associated sensor region 72. If the pupil moves to pupil position 50b, registration of the "+" transferred images 66 with their associated lenslet may again by provided using the pupil location data from the pupil camera 52.

Figure 8A:
FIGS. 8A and 8B schematically illustrate tilt of the eye relative to a fixation target, and a method for correcting the wavefront sensor data by measurement of the tilt.
Figure 8B:
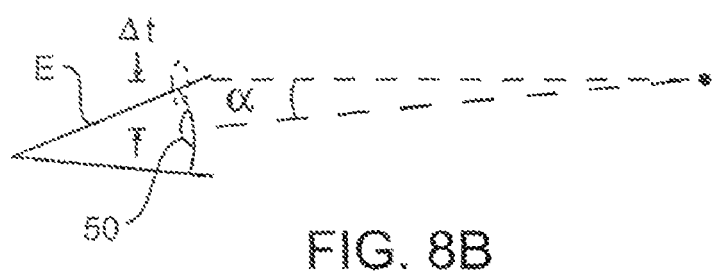

Referring now to FIGS. 8A and 8B, the position of the pupil and eye are also important for accurate determination of wavefront data. Typically, a patient helps maintain alignment of eye E with the wavefront sensor system by fixating on a target 100. However, translation of the eye E from an initial position (as shown in FIG. 8A) to a new position (as shown in FIG. 8B) can induce a displacement angle (i.e., tip or tilt) in the eye E (and hence, in the optical tissues) even though the patient maintains proper fixation on the target. Fortunately, a displacement angle α may again be determined by reference to the information provided by pupil camera 52, as the pupil camera can indicate both the magnitude and direction of a translation Δt. Such displacement angle compensation calculations may significantly facilitate obtaining accurate and repeatable elevation maps from the wavefront sensor data.

Figure 9:
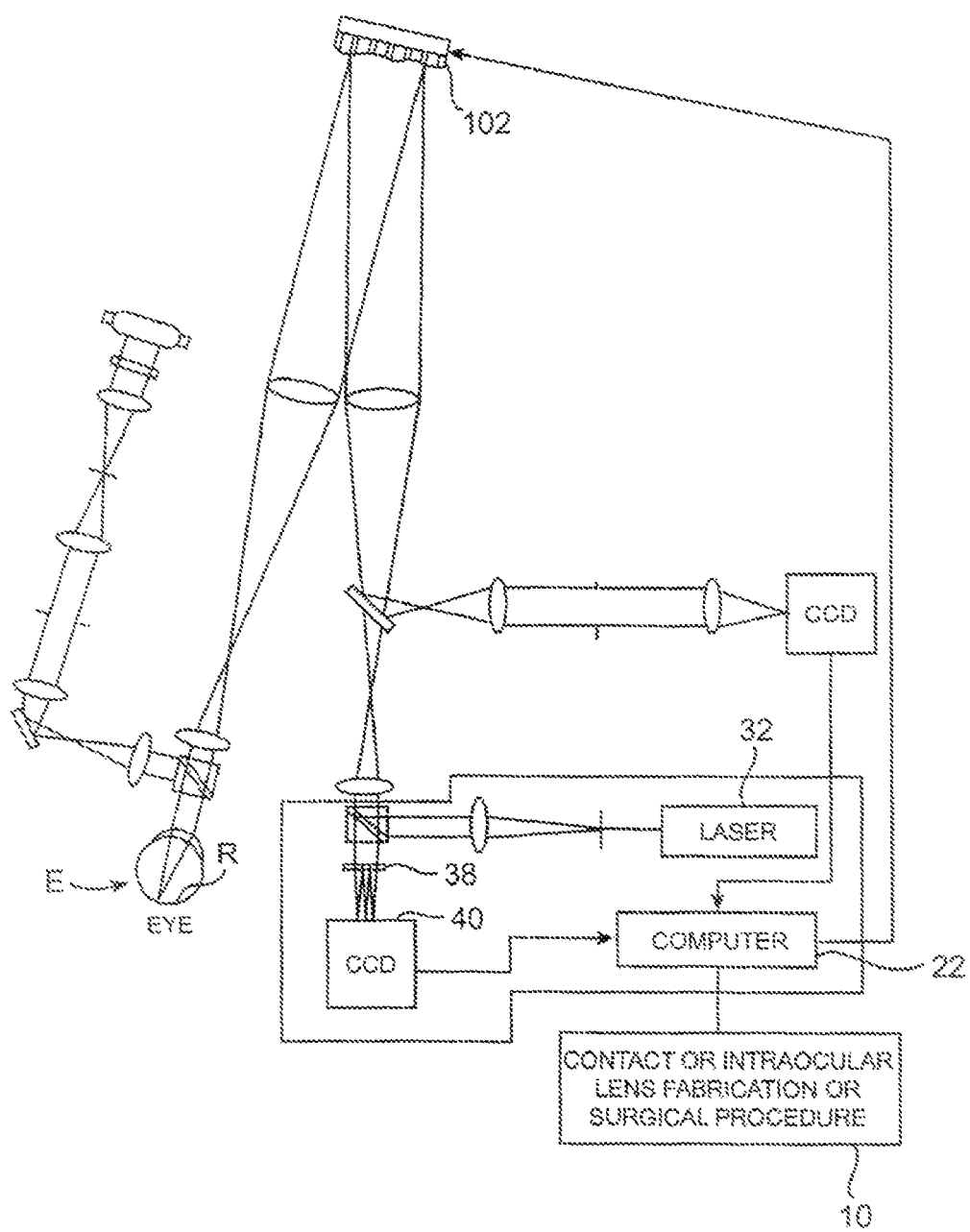
FIG. 9 schematically illustrates an alternative wavefront sensor system suitable for use with the method of the present invention.

An alternative embodiment of a wavefront sensor system which would benefit from the direct ablation treatment program derivation of the present invention is illustrated in FIG. 9. The major components of the system of FIG. 9 are similar to those of FIG. 2. Additionally, FIG. 9 includes an adaptive optical element 102 in the form of a deformable mirror. The source image is reflected from deformable mirror 102 during transmission to retina R, and the deformable mirror is also along the optical path used to form the transmitted image between retina R and imaging sensor 40. Deformable mirror 102 can be controllably deformed to limit distortion of the image formed on the retina, and may enhance the accuracy of the wavefront data. The structure and use of the system of FIG. 9 are more fully described in U.S. Pat. No. 6,095,651, the full disclosure of which his incorporated herein by reference.

In a further embodiment, a WAVESCAN® wavefront system available from VISX, Incorporated of Santa Clara, Calif., may be used. The system may optionally employ a deformable mirror as described in U.S. Pat. No. 6,155,684, the full disclosure of which is herein incorporated by reference.

Figure 10:
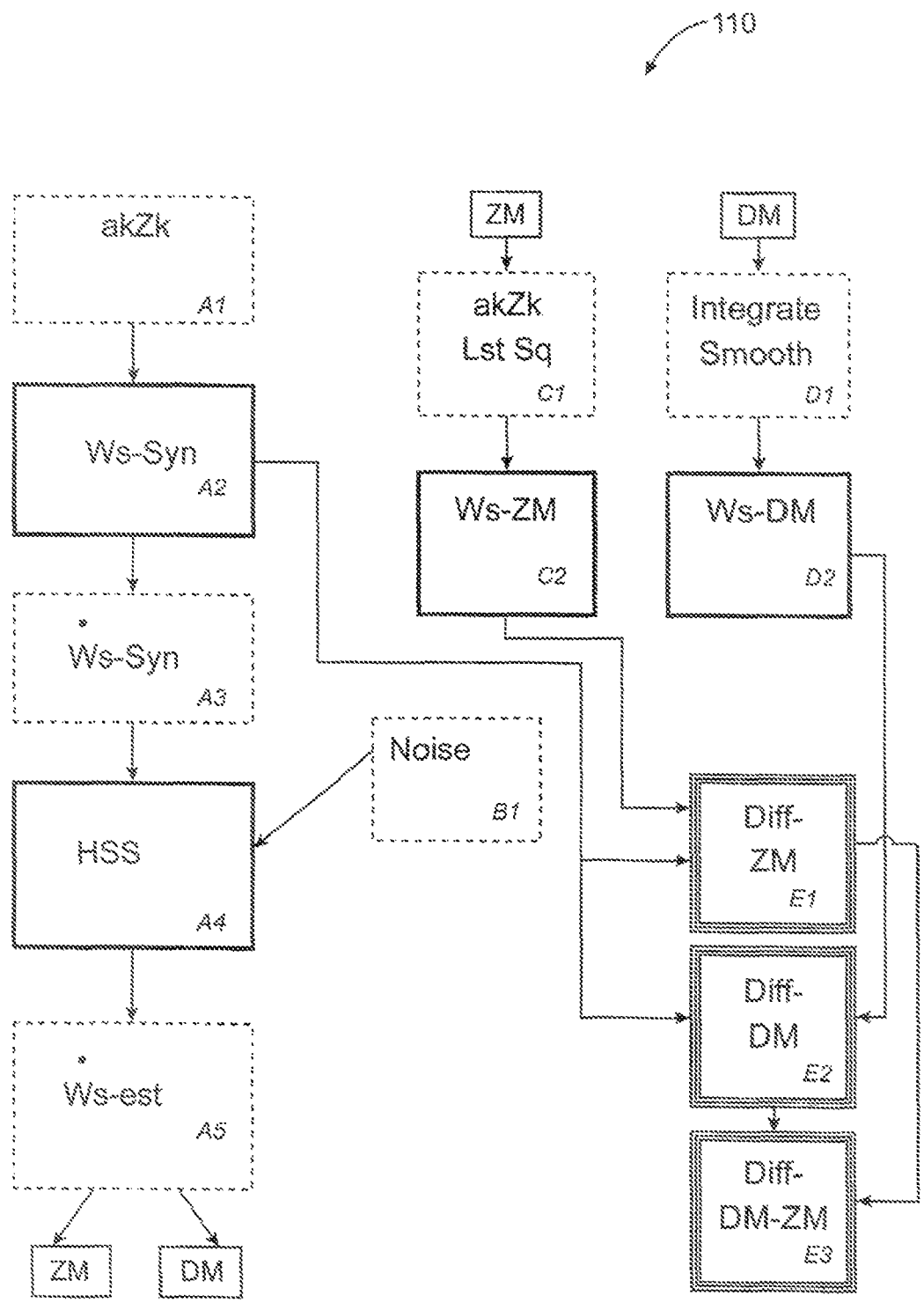
FIG. 10 is a flow chart of a computer program for a wavefront simulation study to determine the accuracy of direct calculation of wavefront elevation and correction maps from wavefront sensor data.

A flow chart for a wavefront simulation study computer program and method 110 is illustrated in FIG. 10. In simulation 110, Hartmann-Shack data and gradients are artificially simulated in a synthesis subroutine A1-A5. Noise may be added to the simulated Hartmann-Shack data in subroutine B1, and the wavefront may be calculated from the synthesized Hartmann-Shack data using the Zernike method subroutine C1, C2. This calculated wavefront may be compared to one calculated using the direct method by a direct calculation subroutine D1, D2, and the differences between the wavefronts may be determined in a comparison subroutine E1-E3.

The synthesis program begins by entering vectors of the Zernike polynomials Zk in step A1. From the Zernike polynomials, a synthetic wavefront may be calculated in step A2, and a synthetic gradient can be calculated in step A3. Computed Hartmann-Shack sensor spot diagrams can be calculated in step A4 from the synthetic gradient and the optical system characteristics. Noise can be artificially added (with the noise optionally based on differences between known reference surfaces and their associated Hartmann-Shack sensor data), in Step B1, to provide a synthetic Hartmann-Shack sensor spot diagram in step A4. Gradients can be estimated from this spot diagram in step A5.

To calculate the associated wavefront from the synthetic Hartmann-Shack gradient array using Zernike method ZM, a least squares fit analysis may be used to determine appropriate coefficients ak of the Zernike polynomials Zk in step C1. The wavefront from this Zernike method may then be calculated in step C2.

For comparison with this calculated Zernike method wavefront, a direct method DM calculation may be performed by integrating the synthetic Hartmann-Shack gradient array in step D1 as described hereinabove, and optionally by smoothing the data using any of a variety of known techniques. This allows calculation of the direct method wavefront in step D2.

The difference between the Zernike method wavefront and the originally synthesized wavefront can be calculated in step E1, and a similar difference between the direct method wavefront and the original synthetic wavefront may be calculated in step E2. A comparison of these two calculated wavefronts can be generated in step E3, with the differences generally being computed using root mean square differences, and the final comparison being between the Zernike method wavefront and the direct method wavefront.

FIG. 11A graphically illustrates a synthetically calculated surface having, for example, a calculated astigmatism of three diopters and a spherical error of +12 diopters. FIG. 11D is a topographical representation of this surface.

Using the simulation study program 110 of FIG. 10, a direct method DM calculation was performed as described to derive a calculated direct method surface as shown in FIGS. 11B and 11E. The differences between the original surface and the direct method surface are graphically illustrated in FIGS. 11C and 11F. These figures generally illustrate a technique that may be employed to characterize a direct method embodiment as illustrated above.

Work in connection with the present invention has shown that proper selection of appropriate Zernike polynomials may facilitate calculations using the methods described hereinabove. Specifically, low order Zernike polynomial coefficients are known to have a large impact on visual acuity. While a large number of additional Zernike polynomials may be considered, selecting appropriate medium order Zernike polynomials for analysis may be sufficiently accurate for real-world applications. As used herein, medium order Zernike polynomials include polynomials having j indices from 6 to 14. By, for example, including only the low order Zernike polynomials and the named medium order Zernike polynomials listed in FIG. 12, a computer model of an optical surface having sufficient accuracy for refractive correction purposes may be determined.

The shape of tissue removed may be readily calculated using the concepts above. Typically, light rays are adjusted to focus at a desirable distance, such as an infinite distance, a shorter distance (such as a third of a meter in the case of older patients desiring amelioration of presbyopia), and/or at a plurality of distances (when a multifocal correction is desired). The light rays refracted by the eye will often be adjusted to refract to a desired orientation. This adjustment may be made by deriving the ablation shape so as to change the slope of the surface of the cornea by ablating tissue so that the gradient of the light ray is directed to the desired focus, for example, at an infinite distance. This calculation is readily made with reference to Snell's law, which is well-known. Once the desired slopes of the surface of the cornea are known, the laser is programmed to ablate a desired shape as described above.

An alternate technique for calculating the shape of the tissue to remove is to derive the desired ablation shape from an optical surface error directly calculated as described above. In such cases, tissue can be removed to adjust the optical surface to a desired shape. The relationship between the depth of material removed and a corresponding change in the optical surface is related to the index of refraction of the material removed. For example, the depth of material to be removed can be calculated by dividing the optical tissue surface map by the quantity (n−1) where n is the index of refraction of the cornea. This relation is simply an application of Fermat's principal of least time, known for over 300 years. One embodiment of a technique for such a calculation is also described in U.S. Pat. No. 6,271,914, the full disclosure of which is herein incorporated by reference.

Figure 13:
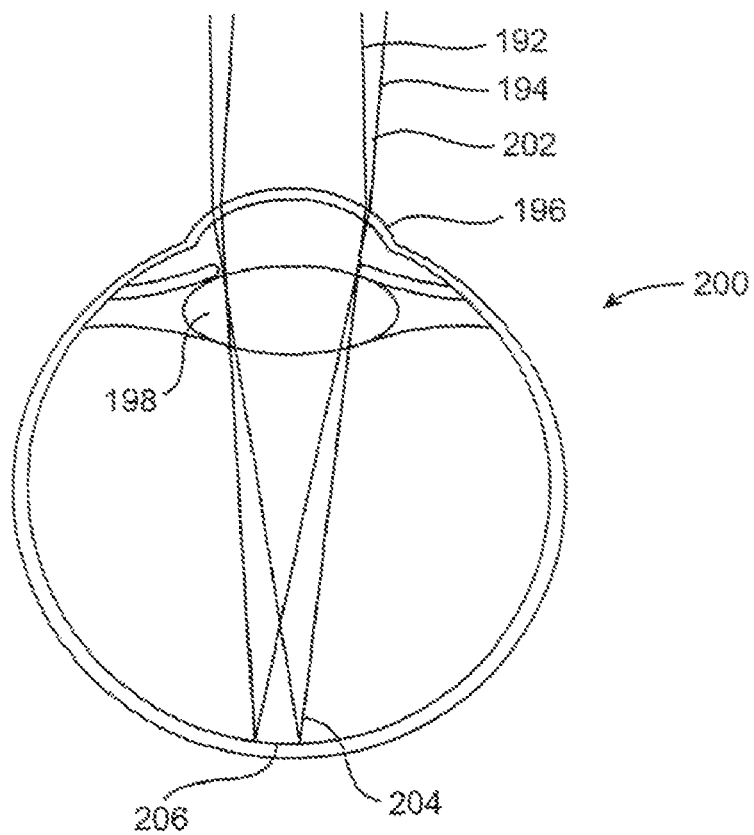
FIG. 13 illustrates a method for detecting a source of an aberration of an eye from among a cornea, lens and retina.

In another embodiment, a plurality of optical tissue surface measurements are taken to obtain a tomographic wavefront error map. The tomographic information describes an optical tissue surface as a composite of localized optical tissue surfaces at different depths inside the eye. With this technique it is possible to determine whether an aberration is caused by a cornea 196, a lens 198 or other tissue structure inside an eye 200 as shown in FIG. 13. This information may be used to decide whether to treat a particular aberration with a laser ablation procedure as described above. Treatment efficacy may be enhanced by selectively treating some portion of the aberrations of the eye, the aberrations selected for treatment comprising only a subset of the total aberrations of the eye. Such selection of aberrations for treatment may be effected by determining a tissue structure corresponding to an aberration and/or an order of the aberration. The selected aberrations are combined to form optical treatment surface, and the selected aberrations are treated by appropriately ablating a shape into the cornea that corrects the aberrations selected for treatment in the optical treatment surface.

Figure 14:
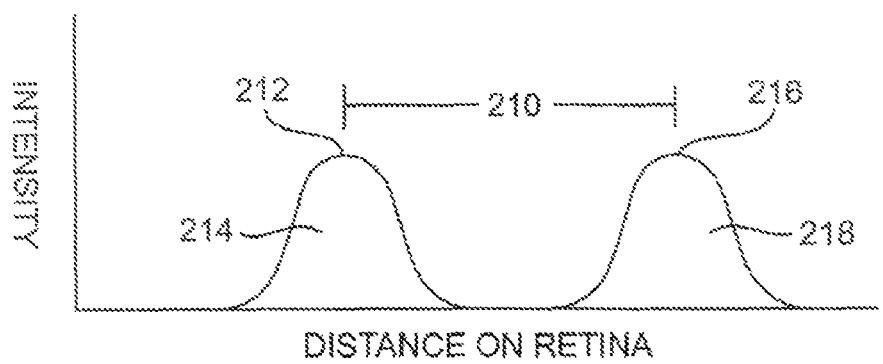
FIG. 14 illustrates two sequential spots of light illuminating a retina of an eye for use in the method of FIG. 13.

Several sequential optical tissue surface measurements are taken. A first light path 192 and a second light path 194 of the sequential measurements are angularly deflected relative to each other by an angle 202 as shown in FIG. 13. A light structure, preferably a spot 204, is formed on the retina 206. The light structure formed on the retina is displaced by a distance on the retina relative to a previous position of the structure during a previous measurement. A first light structure formed on the retina may be sufficiently displaced from a second light structure formed on the retina so that a first feature of the first structure is resolvable from a second feature of the second structure. For example, if the spot has an energy intensity peak, the spots are sufficiently separated by a distance 210 so that a first peak 212 of a first spot 214 is resolvable from a second peak 216 of a spot 218 as shown in FIG. 14. The light structures are positioned sequentially on the retina, and a sequential series of gradient arrays are obtained.

Figure 15:
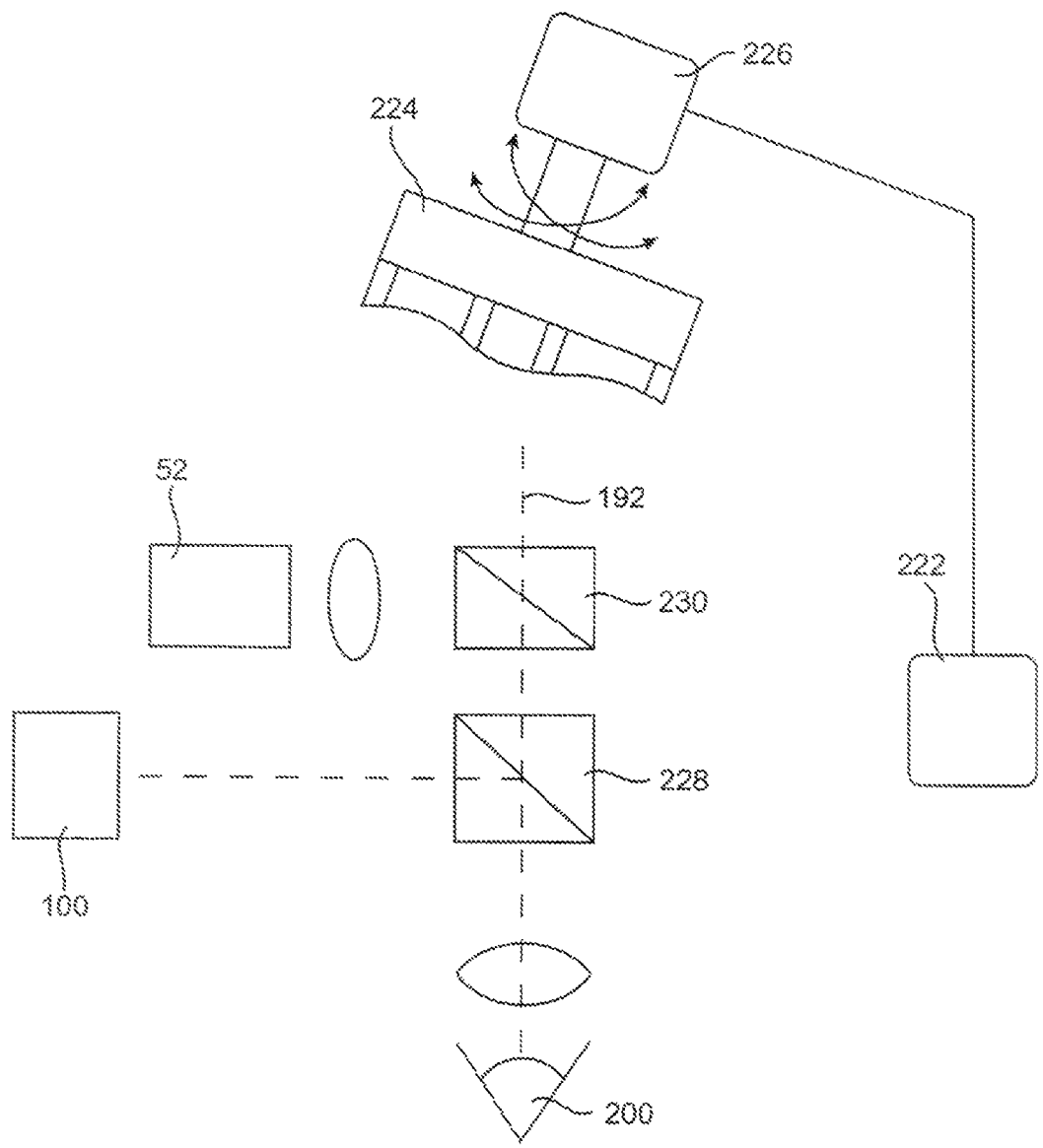
FIG. 15 illustrates a wavefront measurement system used to obtain tomographic information of a wavefront error map of an eye.

As shown in FIG. 15, the eye 200 maintains fixation on a visible fixation target 100 as described above while the light paths of the measurements are angularly deflected relative to the fixation target. Preferably, the fixation target 100 is adjusted so that the accommodation of the eye is relaxed. However, it may be desirable to adjust fixation target 100 to induce the eye to accommodate. During accommodation, the aberrations of the eye may change. Inducing accommodation during measurements of the eye may help localize an aberration to a tissue structure of the eye. The optical axis of the eye is aligned with a pupil camera 52 as described above while the eye fixates on the fixation target. The fixation target 100 and pupil camera 52 are optically coupled to a measurement path 192 by beam splitters 228 and 230 respectively. A deformable mirror 224 as described above may be tilted to discrete angular orientations between sequential measurements to deflect the angular orientation of the measurement path and the position of a light structure formed on the retina. Tilting of mirror 224 may be effected by a command from processor 222 as described above, or by mounting mirror 224 on a gimbal 226 that is under computer control. Items already described above, such as a lenslet array and imaging sensor, have been omitted from FIG. 15 to avoid prolixity. An alternative technique of deflecting the measurement path of the wavefront sensor relative to the eye is to adjust the position or angular orientation of the eye relative to a fixed measurement path. The position and/or angular orientation of the eye may be varied to produce displacement angles $\alpha$ as illustrated in FIGS. 7C, 8A and 8B. When the bundle of light rays associated with an individual measurement travel through a different region of tissue than a previous measurement, the measured optical surface may change as the measurements are taken, depending upon where the aberrations are located within the eye, thereby allowing an aberration-inducing tissue to be identified.

The amount of angular deflection of the measurement paths is related to the spatial resolution of the wavefront sensor system and the desired tissue depth resolution. The cornea is about 3 mm from the lens over the optically used portion of the cornea, and the position of the cornea relative to the lens along the measurement path is changed during the sequential measurements. For a lenslet array having a spacing of 0.4 mm between lenslets, the corresponding spatial frequency is 2.5 cycles per mm. Applying the Nyquist sampling criteria, the maximum resolvable spatial frequency is half of the sampling frequency. For a spacing of 0.4 mm between lenslets the maximum resolvable frequency is about 1.25 cycles per mm, or 0.8 mm per cycle. For a lenslet array having a spacing of 0.1 mm between lenslets the maximum resolvable frequency is about 5 cycles per mm or 0.2 mm per cycle. To obtain a readily resolvable change in the optical tissue surface, an angular deflection of measurement path should move a position of the cornea relative to a position of the lens by at least about 0.1 mm, more preferably about 0.2 mm, even more preferably about 0.4 mm and ideally about 0.8 mm between any two of the sequential measurements. The corresponding angular deflections are at least about 2 degrees, more preferably about 4 degrees, even more preferably about 8 degrees and ideally about 16 degrees.

Data from several angular orientations are sequentially gathered and stored in a memory of processor 222. The accuracy of the arrays is checked as described above. For each measurement, the optical tissue surface is expressed in polynomial form as a Zernike polynomial having p terms of complete radial degree and order. The wavefront W along the optical axis of the eye is calculated from the equation:

$$W = M \cdot L = M \cdot \begin{bmatrix} L1 \\ L2 \\ L3 \\ \cdots \\ Ln \end{bmatrix}$$

Vector L has np dimensions and corresponds to the wavefronts measured at different sequential positions from measurement 1 up to measurement n. M is the desired tomographic matrix and is preferably solved row by row using the singular value decomposition method. One suitable technique for tomographic measurements of starlight wavefronts is described in Nature, pages 54 to 56, vol. 403, January 2000, the full disclosure of which is incorporated herein by reference. The desired tomographic matrix, M, is related to the localized optical tissue surfaces at varying layers of the eye and can be used to calculate the localized optical tissue surface at layers of the eye.

Figure 15A:
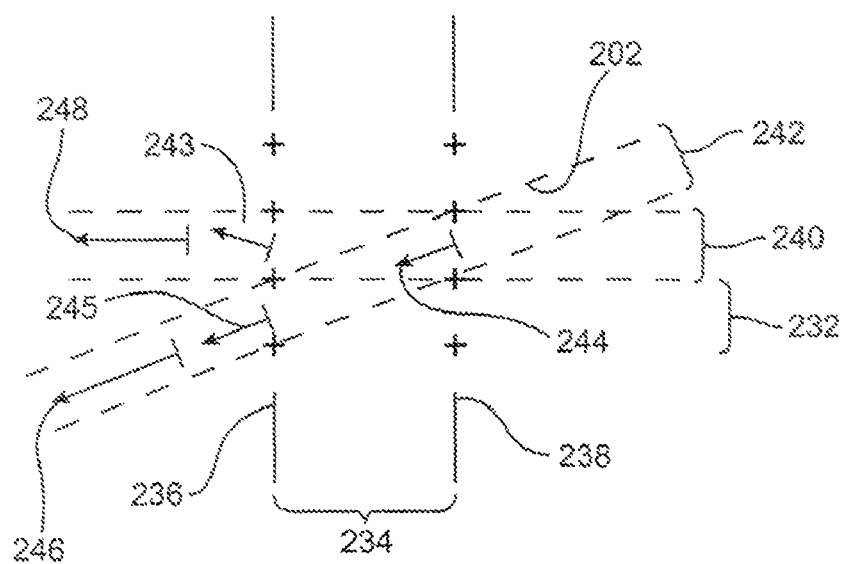
FIG. 15A illustrates overlapping measurement paths at a cornea tissue layer and lens tissue layer of an eye.

Alternatively, the localized optical tissue surfaces may be determined by direct integration. The gradients corresponding to the different layers of the eye are determined from the sequentially gathered data arrays and the corresponding angular deflections of the measurement path. Once the gradients of each layer have been determined, the localized optical tissue surface at each layer of the eye is solved by directly integrating the gradients as described above. Preferably, the measurement path angles are deflected by an amount corresponding to an integer multiple of the sampling period of the paths of the measured gradients at each tissue layer as shown in FIG. 15A. For example, if the lenslet spacing is a distance 232 of 0.4 mm and a separation 234 of the cornea layer 236 and lens layer 238 is about 3 mm, then the deflection angle 202 is preferably about 8 degrees between measurements. As can be seen in FIG. 15A the sampling period distance 232, deflection angle 202, and distance 234 produce a complete overlap of first measured gradient path 240 and second measured gradient path 242 at cornea layer 236 and lens layer 238, respectively. As used herein, the term tissue layer and/or structure may be used to encompass several tissue layers and/or structures within a single layer. For example, the crystalline lens of the eye is a gradient index lens comprising several tissue layers. As used herein, the localized optical tissue surface of the lens may include several layers of the lens tissue.

As shown in FIG. 15A, the overlap of the measured gradient paths 240 and 242 is an integer multiple of one. The localized tissue gradients 242, 244 and 245 are determined from the measured gradients 246, 248, and other measured gradients not shown to avoid prolixity. A measured gradient 246 is the sum of localized tissue gradients 244 and 245 along the measured gradient path 242. A sufficient number of gradients are measured at different deflection angles to uniquely determine the localized tissue gradients. This system preferably uses more than two tissue layers, and the calculation of local gradients can be extended to additional tissue layers.

After the localized optical tissue surfaces corresponding to different layers of the eye have been determined, the aberrations for treatment are selected. Preferably the aberrations for treatment are determined by selecting both an order of the aberration and a corresponding tissue of the aberration inside the eye. The order of an aberration may be assigned a numeric value such as zero, first, second, third, etc. Turning to FIG. 12, the second column with the heading n(ρ) list a numeric value corresponding to an order of several Zernike polynomial terms. The aberrations may be characterized and ordered by other appropriate characterization systems besides Zernike polynomials. For example, the aberrations of the optical tissue surface may be characterized by the terms of classic Seidel aberrations, or also as biconic surfaces with a residual optical surface corresponding to shape of the aberrations; in these latter cases the aberrations are appropriately assigned an order. In the case of localized optical tissue surfaces obtained by direct integration as described above, each localized surface may be considered as an aberration and assigned any desirable arbitrary order, for example 3rd order. A patient may have an aberration at a layer of the eye corresponding to a tissue of the lens. If this lenticular aberration corresponds to second order astigmatism, it is generally acceptable to correct this lenticular astigmatism by ablating a corresponding astigmatic shape in the cornea that corrects for second order astigmatism. However, if the lenticular aberration corresponds to a more irregular shape such as third order trefoil, it may be undesirable to ablate a cornea to correct a third order aberration of the lens. Therefore, a third order aberration corresponding to the lens of the eye is not selected for treatment while the second order aberration corresponding to the lens of the eye is selected for treatment. Further, it is generally desirable to treat all aberrations of the cornea of the eye. Hence, both third order trefoil and second order astigmatic aberrations are selected for treatment if they correspond to the cornea of the eye. The aberrations from the different layers of the eye that are selected for treatment are combined to form an optical treatment surface.

Figure 16:
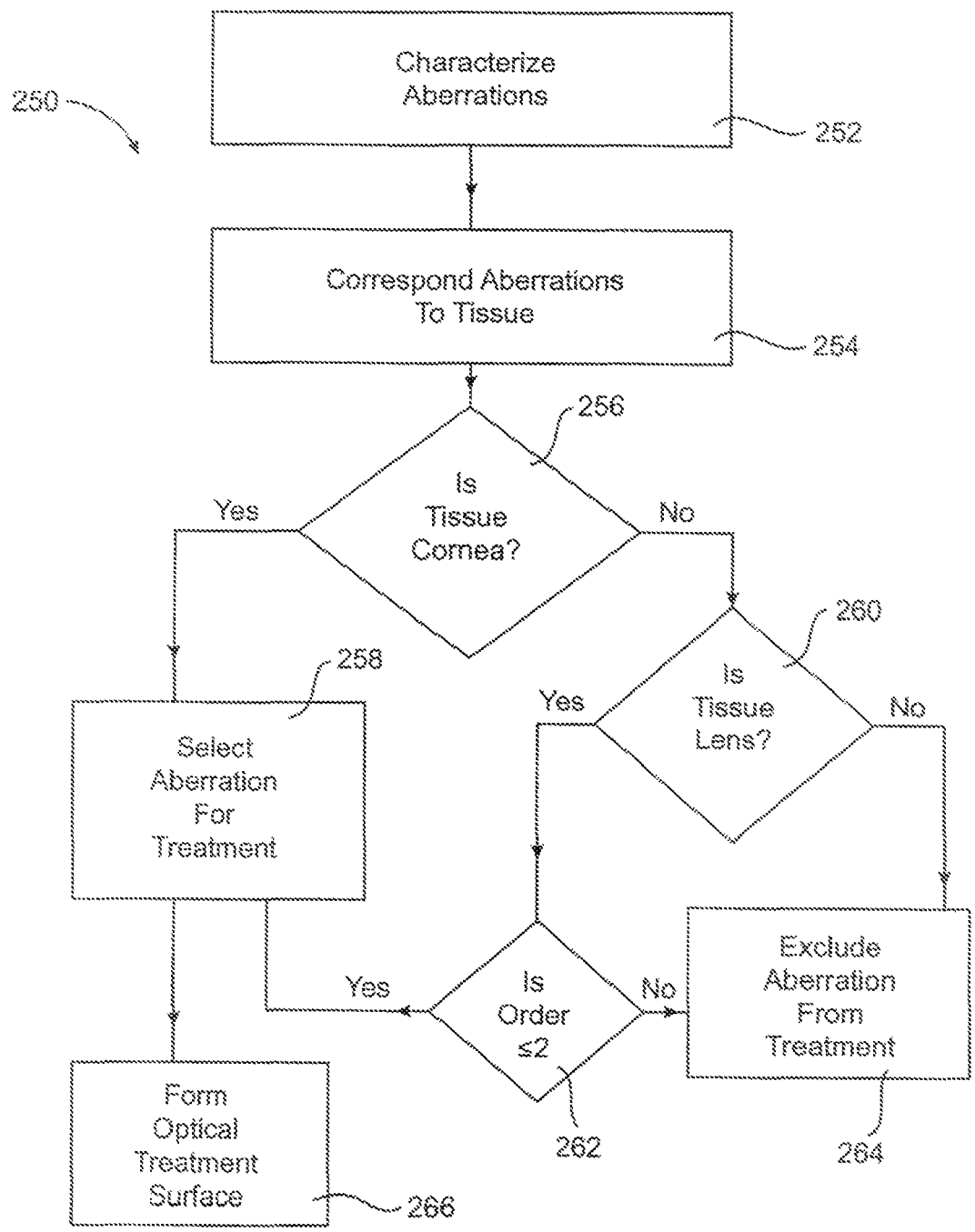
FIG. 16 illustrates a flow chart used to select an aberration for treatment in response to a tissue structure and an order of the aberration.

A flow chart 250 describing the method of selecting aberrations is described in FIG. 16. This flow chart is preferably implemented by a set of machine readable instructions read by a processor 222. The aberrations of a localized optical tissue surface are characterized and assigned an order at 252. The tissue structure corresponding the localized aberrations is determined at 254. The tissue structure is queried at 256. If the tissue structure is cornea, the aberration is selected for treatment at 260. The tissue structure is tested for corresponding to lens at 260. If the tissue structure corresponds to the lens, then the order of the aberration is tested at 262. If the order of the aberration is less than or equal to two, the aberration is selected for treatment at 258. If the order of the aberration is greater than two, then the aberration is excluded from treatment at 264. If the aberration does not correspond to a tissue structure of either cornea or lens, the aberration may be caused by measurement error and is excluded from treatment. Adding the aberrations selected for treatment forms the optical treatment surface at 266. The shape of tissue to be removed from the eye is calculated from the optical treatment surface in a manner similar to the optical tissue surface as described above. The cornea of the eye is then ablated to correct the aberrations of the optical treatment surface as described above.

The tomographic technique described above has the advantage of providing a better estimate of the wavefront map of the eye along the optical axis of the eye. Therefore, the technique of deflecting a measurement path of a wavefront sensor during a series of sequential measurements, as described above, may be employed to more accurately measure a wavefront map of an eye.

While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY TECHNOLOGIES of Bellaire, Tex., WAVELIGHT of Erlangen, Germany, and NIDEK, INC. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to lasers. Therefore, the scope of the present invention is limited solely by the appended claims.

What is claimed is:

1. A method of determining an accuracy of a gradient array in an optical tissue measurement comprising:
    transmitting an image through the optical tissue;
    determining local gradients of the array across the optical tissue from the transmitted image;
    integrating along a closed integration path across a portion of the array; and
    determining the accuracy of the gradient array based on the integration,
    wherein the integration is performed so as to map an error-correcting change in optical tissues.

2. The method of claim 1, further comprising:
    calculating a change in elevation along the closed integration path across the portion of the array.

3. The method of claim 1 wherein, the closed integration path comprises:
    a common starting point, a common ending point, a first integration path connecting the common starting point to the common ending point, and a second integration path connecting the common starting point to the common ending point, the first and second integration paths being different.

4. The method of claim 1, further comprising transmitting a source image from a light source posteriorly through the optical tissues and onto the retina to define the image, wherein the image is transmitted posteriorly through a central region of the cornea, the central region having a size which is significantly less than a pupil size of the eye, and wherein the image is transmitted from the retina anteriorly through the optical tissues.

5. The method of claim 4, wherein the image is transmitted by the optical tissues as a plurality of beamlets, wherein each gradient corresponds to an associated portion of an optical surface such that each beamlet is transmitted through the optical tissue according to the corresponding gradient.

6. The method of claim 1 wherein the mapping step comprises deriving a proposed change in the optical tissue surface elevations so as to effect a desired change in optical properties of the eye, and further comprising modifying the optical tissue surface according to the proposed change by laser ablation.

7. The method of claim 1, wherein the closed integration path extends from a first center of a first portion of the optical surface to a second center of a second portion of the optical surface, from the second center to a third center of a third portion of the optical surface, and from the third center back to the first center, the first, second and third portions of the optical surface corresponding to the first, second and third gradients of the gradient array, respectively.

8. The method of claim 1, wherein the closed integration path extends from an initial location corresponding to a position between a first gradient array element and a second gradient array element, the path crossing a first portion of the optical surface corresponding to the second gradient array element, a second portion of the optical surface corresponding to a third gradient array element, and a third portion of the optical surface corresponding to a fourth gradient array element before returning back to the initial location.

9. The method of claim 1, wherein an elevation map is generated directly in the mapping step without deriving coefficients of a series expansion mathematically approximating the optical surface.

* * * * *